US007834160B2

United States Patent
Okuda et al.

(10) Patent No.: US 7,834,160 B2
(45) Date of Patent: Nov. 16, 2010

(54) PROCESS FOR PRODUCING ZINC OXIDE-PROTEIN COMPLEX

(75) Inventors: Mitsuhiro Okuda, Osaka (JP); Kazuaki Nishio, Osaka (JP); Ichiro Yamashita, Nara (JP)

(73) Assignee: Panasonic Corporation, Osaka (JP)

( * ) Notice: Subject to any disclaimer, the term of this patent is extended or adjusted under 35 U.S.C. 154(b) by 562 days.

(21) Appl. No.: 11/508,261

(22) Filed: Aug. 23, 2006

(65) Prior Publication Data

US 2006/0287511 A1 Dec. 21, 2006

Related U.S. Application Data

(63) Continuation of application No. PCT/JP2006/309477, filed on May 11, 2006.

(30) Foreign Application Priority Data

Jun. 7, 2005 (JP) .............................. 2005-167122

(51) Int. Cl.
C07K 17/00 (2006.01)
H01L 25/00 (2006.01)
(52) U.S. Cl. .......................................... 530/400; 438/1
(58) Field of Classification Search ....................... None
See application file for complete search history.

(56) References Cited

U.S. PATENT DOCUMENTS 6,838,386 B2 * 1/2005 Yamashita .................. 438/706
7,223,847 B2 * 5/2007 Yamashita .................. 530/400
2004/0110347 A1 6/2004 Yamashita
2004/0158047 A1 8/2004 Yamashita
2004/0197884 A1 10/2004 Okuda et al.

FOREIGN PATENT DOCUMENTS

| EP | 1 433 743 A1 | 6/2004 |
| JP | 04-507255 | 12/1992 |
| JP | 2003-86715 A | 3/2003 |
| JP | 2003-113198 A | 4/2003 |
| WO | WO 91/02704 | 3/1991 |
| WO | WO 03/099708 A1 | 12/2003 |

OTHER PUBLICATIONS

Daniel Price, et al., "Ferritin: A zinc detoxicant and a zinc ion donor," Proc. Natl. Acad. Sci., May 1982, pp. 3116-3119, vol. 79.
Mauricio Ortega-Lopez, "Improved efficiency of the chemical bath deposition method during growth of ZnO thin films," Materials Research Bulletin, 2003, pp. 1241-1248, vol. 28 (abstract only).

* cited by examiner

*Primary Examiner*—Anish Gupta
*Assistant Examiner*—Ronald T Niebauer
(74) *Attorney, Agent, or Firm*—McDermott Will & Emery LLP

(57) ABSTRACT

An object of the present invention is to obtain a zinc oxide-protein complex which can be a source of nanoparticles of zinc oxide utilizing a protein having a cavity inside thereof. The process for producing a zinc oxide-protein complex according to the present invention includes a hydrogen peroxide addition step for adding hydrogen peroxide so that the concentration would be 60 mM or greater and 150 mM or less to a buffer containing a protein having a cavity inside thereof such as ferritin, zinc ion, and ammonia.

9 Claims, 4 Drawing Sheets

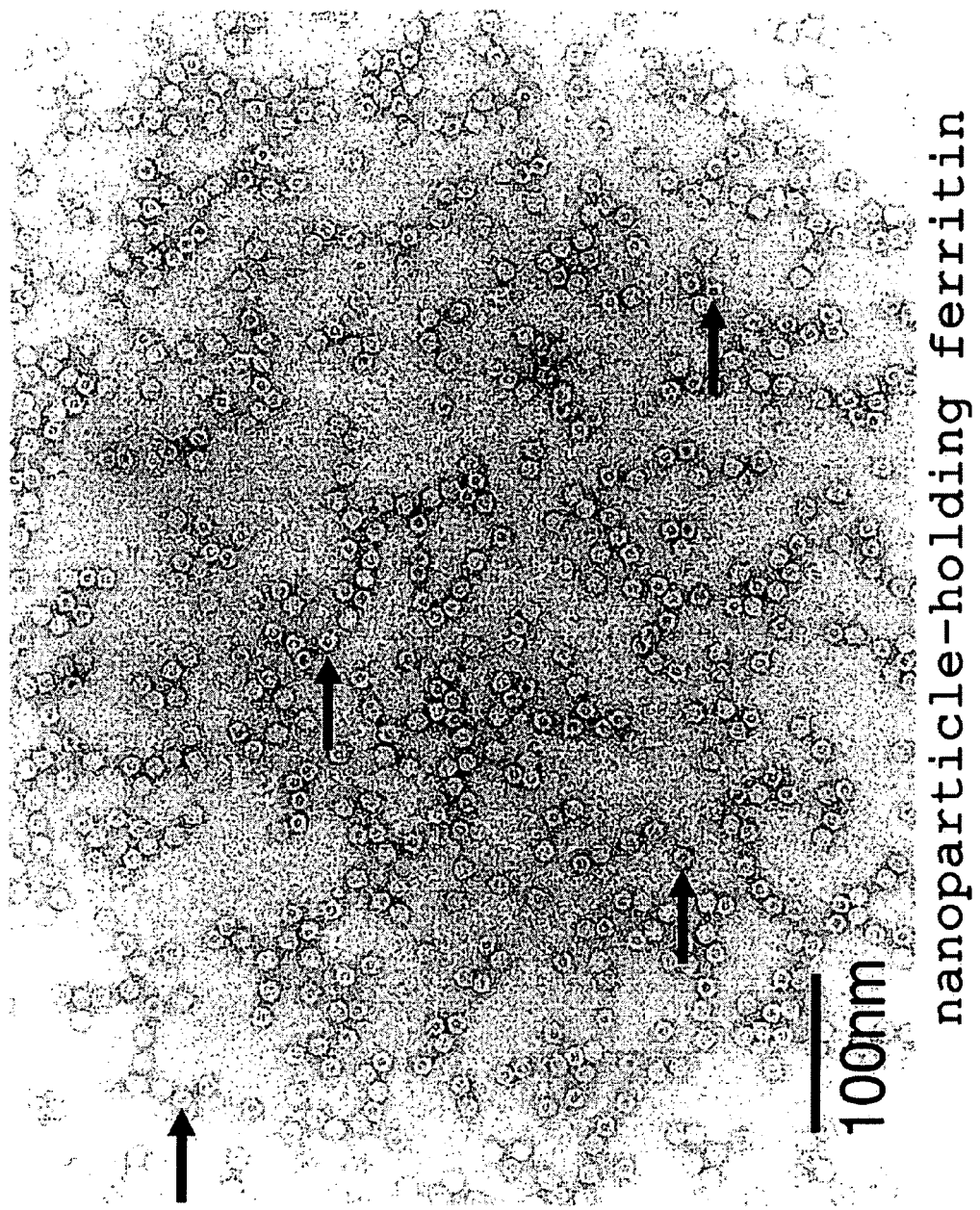
Fig. 4 nanoparticle-holding ferritin

PROCESS FOR PRODUCING ZINC OXIDE-PROTEIN COMPLEX

This is a continuation application under U.S.C 111(a) of pending prior International application No. PCT/JP2006/309477, filed on May 11, 2006, which in turn claims the benefit of Japanese Application No. 2005-167122 filed on Jun. 7, 2005, the disclosures of which Application are incorporated by reference herein.

BACKGROUND OF THE INVENTION

1. Field of the Invention

The present invention relates to a process for producing a zinc oxide-protein complex.

2. Description of the Related Art

Methods of manufacturing a semiconductor apparatus having a dot body such as a quantum dot has been known, as also disclosed in Japanese Patent Provisional Publication No. 2003-86715, D. Price and J. G. Joshi, Proc. Natl. Acad. Sci. USA, 1982, 79, 3116-3119, and Mauricia Ortega-Lopez, Alejandro Avila-Garcia, M. L. Albor-Aguilera and V. M. Sanchez Resendiz, 2003, Materials Research Bulletin 38, p1241-p1248, in which a metal, a metal salt, or a metal compound is filled in a cavity of a protein having a cavity inside thereof such as ferritin; such a protein in a plural number of molecules is arranged in a two-dimensional manner; and thereafter the protein is baked.

A process for filling cobalt oxide in a protein cavity is disclosed in Japanese Patent Provisional Publication No. 2003-113198; and a process for filling a II-VI compound such as CdSe is disclosed in WO 03/099708.

SUMMARY OF THE INVENTION

The present inventor made attempts to fill zinc oxide in a cavity of a protein, i.e., to produce a zinc oxide-protein complex.

However, as presented in Table 2 in Patent Document 2, the zinc oxide-protein complex could not be obtained even though hydrogen peroxide was added to a buffer containing ferritin as a protein having a cavity inside thereof, zinc ion, and ammonia, through using hydrogen peroxide at a concentration of 1 mM to 5 mM (being a typical oxidizing agent).

Proteins are apt to be denatured under the influence of the oxidizing agent.

Therefore, when hydrogen peroxide at a concentration of beyond 5 mM is added, the protein may be denatured, leading to even more difficulties in obtaining a zinc oxide-protein complex.

Although hydrogen peroxide was dared to be used actually at a concentration of 40 mM, no zinc oxide-protein complex could be produced.

The present inventor elaborately investigated on this problem, and consequently found that use of hydrogen peroxide at a concentration of 60 mM or greater and 150 mM or less enables the zinc oxide-protein complex to be obtained. Accordingly, the present invention was accomplished.

An object of the present invention is to provide a process for producing a zinc oxide-protein complex efficiently.

The process for producing a zinc oxide-protein complex according to the present invention which can achieve the object described above has a hydrogen peroxide addition step for adding hydrogen peroxide so that the concentration would be 60 mM or greater and 150 mM or less to a buffer containing a protein having a cavity inside thereof, zinc ion, and ammonia.

A zinc acetate addition step for adding zinc acetate to the buffer is preferably included prior to the hydrogen peroxide addition step.

The concentration of zinc ion after adding the hydrogen peroxide is preferably 1 mM or greater and 20 mM or less.

A zinc nitrate addition step for adding zinc nitrate to the buffer is preferably included prior to the hydrogen peroxide addition step.

The concentration of ammonia after adding the hydrogen peroxide is preferably 8 mM or greater and 360 mM or less.

The buffer is preferably a HEPES buffer.

The buffer has a pH of preferably 6.9 or greater and 10.4 or less.

The ammonia is preferably coordinated with the zinc ion.

Water is preferably further coordinated with the zinc ion.

The protein having a cavity inside thereof is preferably ferritin.

According to the process for producing a zinc oxide-protein complex of the present invention, nanoparticles of zinc oxide having uniform size, can be obtained efficiently.

BRIEF DESCRIPTION OF THE DRAWINGS

FIG. 4 is a transmission electron micrograph illustrating the state of formation of the zinc oxide-protein complex according to an embodiment of the present invention.

DETAILED DESCRIPTION OF THE PREFERRED EMBODIMENTS

Hereinafter, the present invention will be explained in detail.

Herein, "zinc oxide-protein complex" may be merely referred to as "complex".

Furthermore, the concentration is expressed in mM (millimolar, i.e., mmol/L, millimole/liter), however, this means the concentration of the reagent in the resulting buffer, in particular, in the buffer after supplying hydrogen peroxide.

More specifically, when it is referred to as "The concentration of ammonia is 8 mM.", it means that the concentration of ammonia included in the buffer after supplying hydrogen peroxide is 8 mM.

It does not mean that the ammonia concentration in the aqueous ammonia supplied to the buffer is 8 mM. Furthermore, unless otherwise noted, it does not also mean that the aqueous ammonia included in the buffer before supplying hydrogen peroxide is 8 mM.

The same applies to the pH, and unless otherwise noted, the pH refers to that of the buffer after supplying hydrogen peroxide.

(Protein Having a Cavity Inside Thereof)

Examples of the protein having a cavity inside thereof include ferritin.

Naturally occurring ferritin can be obtained from equine spleen by a known method.

The term "ferritin" referred to herein involves naturally occurring (i.e., native) ferritin, as well as genetic recombinant ferritin in which a part of the base is substituted for other base by a genetic recombinant technique. Such genetic recombinant ferritin is illustrated in Japanese Patent Provisional Publication No. 2003-33191.

In light of the efficiency, deleted ferritin of naturally occurring ferritin having deletion of the first to eighth bases from the N-terminal is often used. Such deleted ferritin is also included in the term "ferritin".

Additionally, ferritin without having any metal, metal salt, or metal compound that fills in the cavity inside thereof may be referred to as "apoferritin" for discriminating from the filled ferritin. However, unless explicitly discriminate, the term "ferritin" may involve apoferritin.

Hereinafter, apoferritin will be explained with reference to FIG. 1A and FIG. 1B.

Figure 1A:
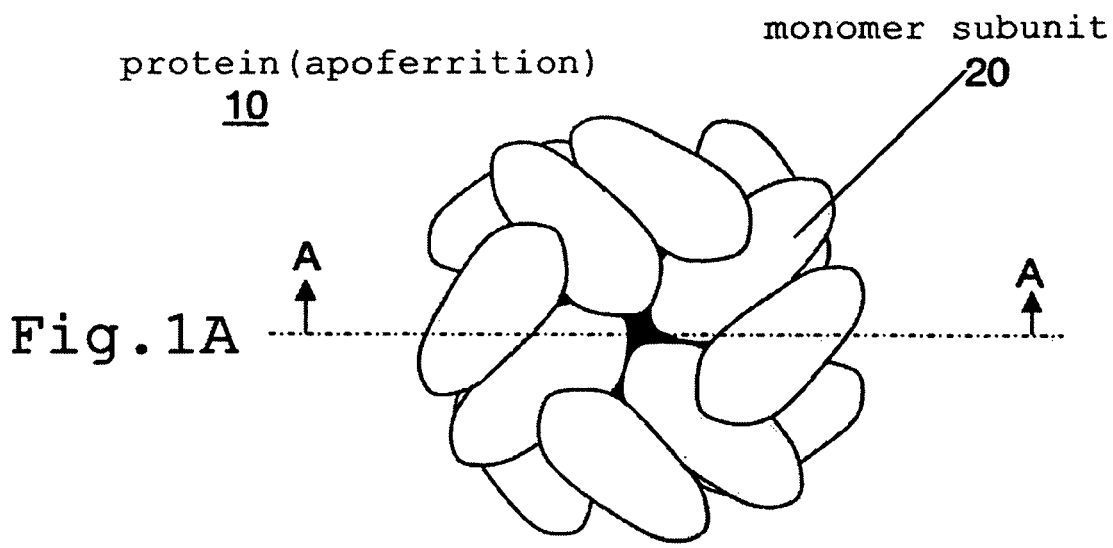
FIG. 1A is a schematic view illustrating the structure of apoferritin.
Figure 1B:
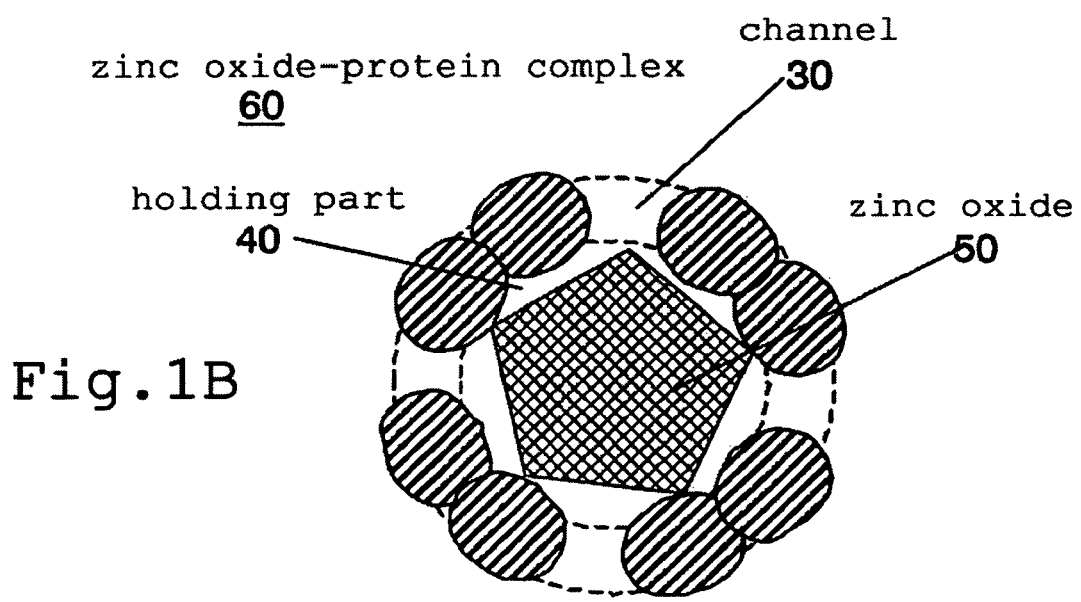
FIG. 1B is a cross-sectional view taken along a line A-A of FIG. 1A.

FIG. 1A is a schematic view illustrating the structure of apoferritin; and FIG. 1B is a cross-sectional view taken along a line A-A of FIG. 1A.

As shown in FIG. 1A, apoferritin 10 is a spherical protein having a molecular weight of about 460,000 formed by assembly of twenty four monomer subunits 20, which is formed of a single polypeptide chain, via a noncovalent bond.

It has a diameter of about 12 nm, and exhibits more excellent thermostability and higher pH stability in comparison with common proteins.

Furthermore, apoferritin 10 has a cavity-shaped holding part 40 having a diameter of about 7 nm at the central portion thereof, as shown in FIG. 1B, which part being connected with the outside via a channel 30.

Hereinafter, a mechanism of formation of nanoparticles in the holding part 40 of apoferritin 10 will be explained by way of an example of iron atoms as may be executed in a living body.

On the surface of the channel 30 that connects between the outside and the inside of the apoferritin 10 is exposed amino acids having a negative charge under conditions of pH 7 to pH 8.

Thus, bivalent iron ions having a positive charge are incorporated into the channel 30 by an electrostatic interaction with the amino acid having a negative charge.

In addition, a number of glutamine acid residues that are amino acid residues having a negative charge at pH 7 to pH 8 are exposed on the inner surface of the holding part 40 of the apoferritin 10, similarly to the inner surface of the channel 30.

Hence, the bivalent iron ions incorporated from the channel 30 are oxidized at a site referred to as ferroxidase center (active center of iron oxidation) that is present within a part of the subunits, and lead to the holding part 40 inside. Then, the iron ions are concentrated by the electrostatic interaction to result in core formation of ferrihydrite ($5Fe_2O_3 \cdot 9H_2O$) crystals.

Thereafter, the iron ions that are incorporated sequentially adhere to the core of the ferrihydrite crystal, and the core including the iron oxide grows to form a nanoparticle including the iron oxide having a diameter of 7 nm in the holding part 40.

Hitherto, nanoparticle-apoferritin complexes have been produced through artificially allowing the metal or metal compound as shown below to be held, using this apoferritin.

For example, manganese, uranium, beryllium, aluminum and zinc may be involved.

Hereinabove, mechanisms of incorporation of iron ions into apoferritin have been explained, and it is believed that other metal ions the introduction of which has been reported so far will follow almost the same mechanism as that of the iron ion.

Also, the diameter of the nanoparticles including such metal or metal compound will be almost equal to the diameter of the holding part 40 of apoferritin, i.e., about 7 nm.

Whether a protein constituted of a single subunit or a protein constituted of multiple subunits, it can be used in stead of apoferritin as long as it has a cavity.

Among them, proteins constituted of subunits having the identical amino acid sequence, or proteins that are recombinant constituted of a single monomer, for example, recombinant ferritin and the like are preferred because these are resistant to denaturation due to their stable structure, and great resistance against oxidizing agents at high concentrations.

The cavity shape of the protein is not limited to spherical, but the protein may have the holding part in a rod shape, ring shape or the like. Examples of the protein include Dps protein and viral proteins.

For example, when the Dps protein (spherical shell-shaped protein having a diameter of 9 nm, and a holding part with a diameter of 4 nm inside thereof) is used, nanoparticles of zinc oxide having a diameter of 4 nm can be produced.

Examples of the viral protein include e.g., CPMV, CCMV, HSV, Rotavirus, Reovirus, LA-1, Polyoma, CaMV, HPV, Ross River, SpV-4, φX174, FHV, HRV-14., Polio and the like.

Among them, viral proteins such as CPMV and CCMV may be preferably used taking into consideration of their ease in handling and shape.

As in the foregoing, nanoparticles of zinc oxide can be formed depending on the shape and size of the cavity-shaped holding part of the used protein, according to this embodiment.

The "nanoparticle" referred to herein is the particle having the size greater than those which are 50 nm or less, and can be present stable as a particle. Examples of them corresponding to the nanoparticle include particles having a diameter of 1 nm to 50 nm.

(Zinc Ion)

The buffer contains a zinc ion.

Origin of the zinc ion is not particularly limited, but can be generally supplied in the form of a metal salt.

In light of the yield, it is preferred that zinc acetate have been supplied to the buffer as also clear from the Experimental Example 4 and Table 4 shown later.

The concentration of the zinc ion is preferably 1 mM or greater and 20 mM or less.

The concentration of the zinc ion being less than 1 mM tends to result in difficulty in formation of the complex due to too low zinc ion concentration.

As is also clear from Experimental Example 3 and Table 3 shown later, the concentration of the zinc ion is most preferably 2 mM. When the concentration is higher than this, the yield can be reduced.

The concentration of the zinc ion beyond 20 mM is not efficient.

In particular, when zinc acetate is used, such a tendency and efficiency may be remarkable.

Zinc nitrate may be also supplied to the buffer although it may be inferior to zinc acetate.

As is also clear from Experimental Example 4 and Table 4 shown later, higher yield is achieved when zinc nitrate is used than the cases in which zinc; sulfate is used.

(Ammonia)

The buffer contains ammonia.

In the present invention, ammonia is believed to coordinate with the zinc ion, as a ligand.

This is also disclosed in WO 03/099708.

The zinc ion may have four ligands, and all of them may be ammonia, or only a part thereof may be ammonia while other ligands being water.

Ammonia may be supplied to the buffer in the form of aqueous ammonia.

As is also clear from Experimental Example 2 and Table 2 shown later the concentration of ammonia is preferably 8 mM or greater and 360 mM or less.

The concentration of ammonia being less than 8 mM tends to result in difficulty in formation of the complex.

The concentration of ammonia beyond 360 mM is not efficient.

(Buffer)

The buffer is not particularly limited, but a HEPES buffer is preferably used.

As is also clear from Experimental Example 2 and Table 2 shown below, the buffer has a pH of preferably 6.9 or greater and 10.4 or less.

The pH being less than 6.9 or beyond 10.4 does not provide a condition desired for ferritin that prefers a weakly basic condition.

(Addition of Hydrogen Peroxide)

The present invention is characterized by the addition of hydrogen peroxide so that the concentration would be 60 mM or greater and 150 mM or less to a buffer containing the protein having a cavity inside thereof as described above (representatively ferritin), zinc ion, and ammonia concentration.

As is also clear from Experimental Example 1 and Table 1 shown later, the concentration of hydrogen peroxide is most desirably 100 mM.

When the concentration of the hydrogen peroxide included in the buffer is less than 60 mM, the complex cannot be formed. Similarly, also when the concentration of hydrogen peroxide included in the buffer is beyond 150 mM, the complex cannot be formed.

The concentration of hydrogen peroxide in the buffer that enables the complex to be formed is 60 mM or greater and 150 mM or less. However, the concentration of hydrogen peroxide included in preferred buffers may be 80 mM or greater and 120 mM or less.

The hydrogen peroxide is supplied to the buffer in the form of an aqueous hydrogen peroxide solution.

After supplying hydrogen peroxide to the buffer, the mixture may be left to stand for 1 day or longer.

Thereafter, the complex can be obtained from the buffer by centrifugal separation or the like.

(Other)

The complex may be preferably obtained while mixing by stirring with a stirrer or the like at a room temperature, or in the temperature range not to cause denaturation of the protein 10 such as apoferritin, for example, at 70° C. or lower.

(Theoretical Description)

The present inventors do not prefer the present invention to be bound by the following theory in any sense, but believe that the mechanism by which the complex is formed may be as described below.

First, negative charge is widely distributed on the surface of the protein. Hence, the zinc compound-introduced into the solution, or positively, charged $Zn^{2+}$ and ammonium ion generated from ammonia may be bound to the negative charge.

Therefore, even though hydrogen peroxide that is an oxidizing agent is going to react with the protein, it cannot be directly reacted to the protein because the protein is protected by the $Zn^{2+}$ and ammonium ion which had been bound on the surface thereof.

Thus, hydrogen peroxide oxidizes $Zn^{2+}$ bound on the surface of the protein to generate trivalent positively charged $Zn^{3+}$ (or an intermediate of Zn).

However, because $Zn^{3+}$ is unstable, it immediately turns back to $Zn^{2+}$.

Furthermore, in turning back to $Zn^{2+}$, $Zn^{3+}$ acts as an oxidizing agent, and oxidizes $Zn^{2+}$ and hydrogen peroxide in the solution.

It is believed that by repeating such a process, denaturation of the protein may be hardly caused because the reaction of the protein with hydrogen peroxide can be prevented even in a solution including hydrogen peroxide added at a high concentration.

To the contrary, in case of the cobalt-protein complex disclosed in Japanese Patent Provisional Publication No. 2003-113198, positively charged $Co^{2+}$ and ammonium ion are bound on the surface of the protein similarly to the case as described above.

Then, hydrogen peroxide similarly oxidizes $Co^{2+}$ to covert into trivalent positively charged $Co^{3+}$.

However, $Co^{3+}$ is so stable that is does not turn back to $Co^{2+}$.

Therefore, $Co^{3+}$ does not act as an oxidizing agent.

Accordingly, in a solution containing hydrogen peroxide at a high concentration, the reaction of hydrogen peroxide to the protein cannot be prevented. Therefore, the protein is readily denatured.

As a result, in case of formation of the cobalt-protein complex, hydrogen peroxide is essential, although it cannot be introduced at a high concentration. The concentration is presumed to be 5 mM.

As in the foregoing, in the present invention, unlike the process in which cobalt is included in the holding part of the protein, the zinc oxide-protein complex can be obtained efficiently by utilizing the characteristics of Zn as an ion effectively by means of ammonia and hydrogen peroxide that is an oxidizing agent.

Consequently, introduction of hydrogen peroxide into a solution at a high concentration of 60 mM or greater and 150 mM or less was enabled, and the zinc oxide-protein complex can be formed in high yield with favorable reproducibility.

Moreover, this mechanism will be explained with reference to the drawing.

Figure 3:
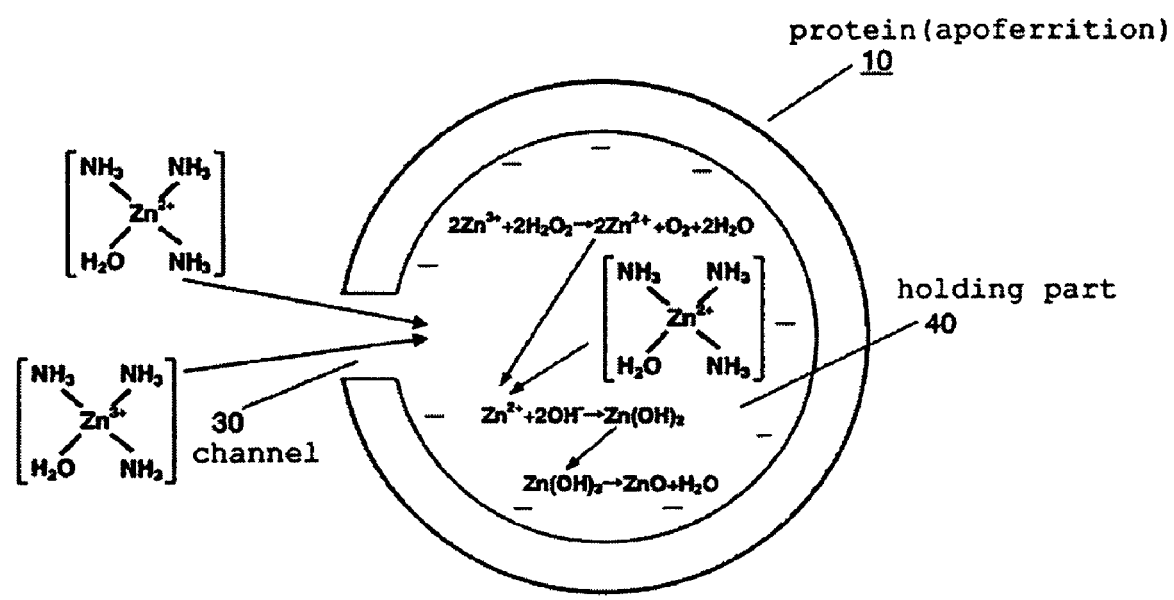
FIG. 3 is a schematic view for illustrating the reaction which is conceived to occur in the production step of the zinc oxide-protein complex according to an embodiment of the present invention.

FIG. 3 is a schematic view for illustrating the mechanism for the formation of the zinc oxide-protein complex.

The protein 10 shown in FIG. 3 is illustrates the protein shown in FIG. 1A and FIG. 1B with simplification, using the same reference sign for the same component.

Under the condition in the adjusted solution, the ammonium ions that exist in a large number and the zinc ions generated from the zinc compound form complex ions of the zinc ion with ammonia, and are stabilized in the state of, for example, a part thereof being substituted for water.

Then, because the surface of the holding part 40 of the protein 10 is negatively charged, the complex ion of the zinc ion with ammonia is incorporated in the holding part 40 by electrostatic interaction through a channel 30.

As a result, the complex ion of the zinc ion with ammonia is concentrated in the holding part 40 of the protein 10 at a high concentration.

Moreover, as also described on the mechanism not to cause denaturation of the protein 10 in hydrogen peroxide at a high concentration, complexions of the trivalent zinc ion having a positive charge with ammonia are similarly formed in the solution, and exist in the solution.

Hence, the trivalent complex ion having a positive charge more readily enters into the holding part 40 of the protein 10 that is negatively charged, in comparison with the bivalent complex ion having a positive charge.

Thus, the zinc ion of the trivalent complex ion having a positive charge incorporated into the holding part 40 of the protein 10 is reduced by hydrogen peroxide into the bivalent positively charge zinc ion.

Furthermore, the bivalent zinc ion concentrated in the holding part 40 of the protein 10 at a high concentration forms zinc hydroxide $(Zn(OH)_2)$ by the hydrogen peroxide.

Then, thus formed zinc hydroxide $(Zn(OH)_2)$ alters into zinc oxide (ZnO), counterpart of the equilibrium state, depending on the elevation of the zinc concentration in the holding part 40 of the protein 10, and the pH value adjusted optimally.

As a result, it is believed that zinc oxide (ZnO) that is insoluble in water is accumulated in the holding part 40 of the protein 10 to form the zinc oxide-protein complex.

As described hereinabove, according to the process for producing a zinc oxide-protein complex of the present invention, even though hydrogen peroxide that may cause denaturation of a protein is introduced at a high concentration, the zinc oxide-protein complex can be formed efficiently without denaturing the protein.

Also, nanoparticles of zinc oxide having a uniform size can be produced with favorable reproducibility from the resulting zinc oxide-protein complex.

EXAMPLES

Hereinafter, the present invention will be explained in more detail with Examples (experimental data).

Example 1

In this Example 1, data of an experiment on the concentration of hydrogen peroxide are demonstrated.

L-chain apoferritin, zinc acetate, and ammonium hydroxide (aqueous ammonia) presented below were added to a HEPES buffer.

50 mg/mL L-chain apoferritin 8 μL
100 mM zinc acetate 40 μL
100 mM aqueous ammonia 320 μL
500 mM HEPES 800 μL
Purified Q water 1016 μL The pH was adjusted by adding sodium hydroxide and aqueous ammonia so that the value became 7.8.

To thus prepared HEPES buffer was added 882 mM hydrogen peroxide so that the concentration after the addition would be as shown in Table 1, and the mixture was stirred.

When the concentration of hydrogen peroxide in the buffer is 100 mM, the pH following the stirring was 6.9.

The HEPES concentration after the addition of hydrogen peroxide was 200 mM; the apoferritin concentration after the addition of hydrogen peroxide was 0.2 mg/mL; the zinc acetate concentration after the addition of hydrogen peroxide was 2 mM; and the ammonia concentration after the addition of hydrogen peroxide was 16 mM. The pH after the addition of hydrogen peroxide was 6.9. Total amount of the buffer was 2 mL. Also in Examples 2 to 4 described later, total amount of the buffer was 2 mL.

Thereafter, the HEPES buffer was left to stand for 24 hours.

Next, the precipitate was removed by centrifugal separation at 3000 rpm for 20 min using a centrifugal separator.

TABLE 1

| Hydrogen peroxide concentration | 40 mM | 60 mM | 80 mM | 100 mM | 120 mM | 150 mM | 200 mM |
|---|---|---|---|---|---|---|---|
| Formation state of zinc oxide-protein complex | X | Δ | ○ | ⊚ | ○ | Δ | X |

("⊚": particularly favorable, "○": favorable, "Δ": permissible, "X": unsuitable)

Table 1 shows the results determined on the formation state of the zinc oxide-protein complex depending on the concentration of hydrogen peroxide.

Reference symbols in the Table represent the proportion of formation of the zinc oxide-protein complex in the total amount of the protein, showing: "⊚" being 80% or greater, "○" being 10% or greater and 80% or less, "Δ" being less than 10%, and "X" being 0% or scarcely formed. These are also true in other Tables.

As shown in Table 1, it is proven that the zinc oxide-protein complex can be formed in the range of 60 mM or greater and 150 mM or less of the hydrogen peroxide included in the buffer.

In other words, denaturation of the protein could be suppressed by using hydrogen peroxide at a concentration that is unexpectedly high judging from conventional examples including Japanese Patent Provisional Publication No. 2003-113198 with favorable efficiency.

In particular, when the concentration of hydrogen peroxide that is an oxidizing agent was set to be 100 mM, formation of the zinc oxide-protein complex in high yield of 90% or greater was found.

FIG. 4 shows a transmission electron micrograph taken in the case of the concentration of hydrogen peroxide being 60 mM.

Ferritin indicated by arrow heads includes zinc oxide.

The way of taking this picture has been already known, however, the explanation will herein follow to make sure.

When apoferritin consisting of the protein alone is observed directly with an electron microscope, nothing can be seen. Thus, apoferritin is stained with a stain referred to as gold glucose. Accordingly, the gold glucose occupies: around the apoferritin, and thus, observation of apoferritin is allowed because the apoferritin part is observed as a white circle, while the part surrounding apoferritin is observed as being black. The gold glucose does not enter into apoferritin.

In the case of ferritin including a core of zinc oxide therein, the core of zinc oxide is seen black at the center of the white circle. More specifically, the observed donut shape shows ferritin, with the white donut part corresponds to the proteinous part of ferritin, and the inside of the donut corresponding to the core of zinc oxide.

Accordingly, number of the donut-shaped ferritin including the core, and number of the white circular apoferritin without having the core were counted. Thus, percentage of ferritin in total number of apoferritin and ferritin observed in the picture was determined on each concentration (The results are shown in Table 1).

Example 2

In this Example 2, data of an experiment on the pH and the concentration of ammonia are demonstrated.

In this Example, the experiment was carried out with separate three regions capable of adjusting both the pH value and ammonia concentration of the solution, as shown below.

In the first region, the solution had a pH value of less than 8.2, and a concentration of ammonia falling within the range of 60 mM or less.

In this range, the solution was prepared in a similar manner to Example 1.

Hydrogen peroxide was mixed into the reaction solution such that the concentration in the solution became 100 mM.

The HEPES concentration after the mixing of hydrogen peroxide was 200 mM; the apoferritin concentration after the mixing of hydrogen peroxide was 0.2 mg/mL; and zinc acetate after the mixing of hydrogen peroxide was 2 mM. The pH was adjusted predominantly by adding sodium hydroxide to the buffer.

In the second region, the solution had a pH value of 8.2 or greater, 10.5 or less, and a concentration of ammonia falling within the range of 60 mM or less.

L-chain apoferritin, zinc acetate, and ammonium hydroxide (aqueous ammonia) presented below were added to a CAPSO buffer.

50 mg/mL L-chain apoferritin 8 μL
100 mM zinc acetate 40 μL
100 mM aqueous ammonia 120 μL
500 mM CAPSO 800 μL
Purified water 1216 μL The pH was adjusted to give the value of 9.4 once by adding sodium hydroxide and aqueous ammonia.

To thus prepared CAPSO buffer was added 882 mM hydrogen peroxide so that the concentration after the addition would be 100 mM, and the mixture was stirred.

When the concentration of hydrogen peroxide in the buffer is 100 mM (added amount: 226 mL), the pH following the stirring was 9.1.

In the third region, the solution had a pH value of 6.5 or greater, 10.5 or less, and a concentration of ammonia falling within the range of beyond 60 mM.

L-chain apoferritin, zinc acetate and ammonium hydroxide (aqueous ammonia), and ammonium chloride presented below were mixed in purified water.

50 mg/mL L-chain apoferritin 8 μL
100 mM zinc nitrate 40 μL
1M-aqueous ammonia 120 μL
2M ammonium chloride 240 μL
Purified water 1366 μL The pH was adjusted to give the value of 9.4 once by adding sodium hydroxide and aqueous ammonia.

To thus prepared CAPSO buffer was added 882 mM hydrogen peroxide so that the concentration after the addition would be 100 mM, and the mixture was stirred.

The CAPSO concentration after the mixing of hydrogen peroxide was 200 mM; the apoferritin concentration after the mixing of hydrogen peroxide was 0.2 mg/mL; the ammonia concentration after the mixing of hydrogen peroxide was 16 mM; and zinc acetate after the mixing of hydrogen peroxide was 2 mM.

The pH was thereafter adjusted predominantly by adding sodium hydroxide.

Then, thus resulting solution was left to stand at room temperature for 24 hours, and the state of formation of the zinc oxide-protein complex was studied.

The evaluation on the state of formation of the zinc oxide-protein complex then was made by observation with a transmission electron microscope (TEM) similarly to Experimental Example 1.

States of formation of the zinc oxide-protein complex after the solutions obtained in the aforementioned three regions were left to stand at room temperature for 24 hours are summarized in Table 2 below. In Table 2, the states of formation of the zinc oxide-protein complex versus the pH value of the solution and ammonia concentration are relatively shown.

TABLE 2

| Ammonia concentration | Final pH of solution | | | | | | | | | | |
|---|---|---|---|---|---|---|---|---|---|---|---|
| | pH 6.9 | pH 7.2 | pH 7.3 | pH 7.4 | pH 8.2 | pH 8.5 | pH 9.0 | pH 9.1 | pH 9.4 | pH 10.1 | pH 10.4 |
| 0 mM | X | X | — | — | — | X | X | — | — | X | X |
| 8 mM | Δ | — | — | — | — | Δ | — | — | — | — | Δ |
| 14 mM | O | — | — | O | — | — | — | — | — | — | — |
| 16 mM | ⊚ | — | — | — | — | — | — | Δ | — | — | — |
| 32 mM | — | O | — | — | — | Δ | — | — | — | — | Δ |
| 40 mM | — | — | O | — | — | — | — | — | — | — | — |
| 50 mM | — | — | — | — | O | O | — | — | O | — | — |
| 60 mM | O | — | — | O | O | ⊚ | ⊚ | ⊚ | O | — | Δ |
| 250 mM | — | — | — | — | O | O | O | — | O | — | — |
| 300 mM | Δ | — | — | — | O | O | Δ | — | — | O | — |
| 360 mM | Δ | — | — | — | — | Δ | Δ | — | — | — | Δ |

("⊚": particularly favorable, "O": favorable, "Δ": permissible, "X": unsuitable, "—": unexamined)

The CAPSO concentration after the mixing of hydrogen peroxide was 200 mM; the apoferritin concentration after the mixing of hydrogen peroxide was 0.2 mg/mL; the ammonia concentration after the mixing of hydrogen peroxide was 16 mM; and zinc acetate after the mixing of hydrogen peroxide was 2 mM.

The pH was thereafter adjusted predominantly by adding sodium hydroxide to the buffer.

As shown in Table 2, it is proven that the zinc oxide-protein complex could be formed in the range of the ammonia concentration being 8 mM or greater, 360 mM or less, and in the range of the pH value of the solution being 6.9 or greater, 10.4 or less.

Moreover, it is proven that the range of the ammonia concentration being 14 mM or greater, 60 mM or less, and the range of the pH value of the solution being 6.9 or greater, 7.4 or less; and the range of the ammonia concentration being 50 mM or greater, 250 mM or less, and the range of the pH value of the solution being 8.2 or greater, 9.4 or less are particularly preferred because the zinc oxide-protein complex could be formed in high yield with favorable reproducibility in such ranges.

Among them, the zinc oxide-protein complex could be obtained in yield of 90% or greater, at the pH value of the solution being approximately 6.9, at the ammonia concentration being 16 mM, at the zinc acetate concentration being 2 mM, apoferritin being 0.2 mg/mL, and at the hydrogen peroxide concentration being 100 mM.

Figure 2:
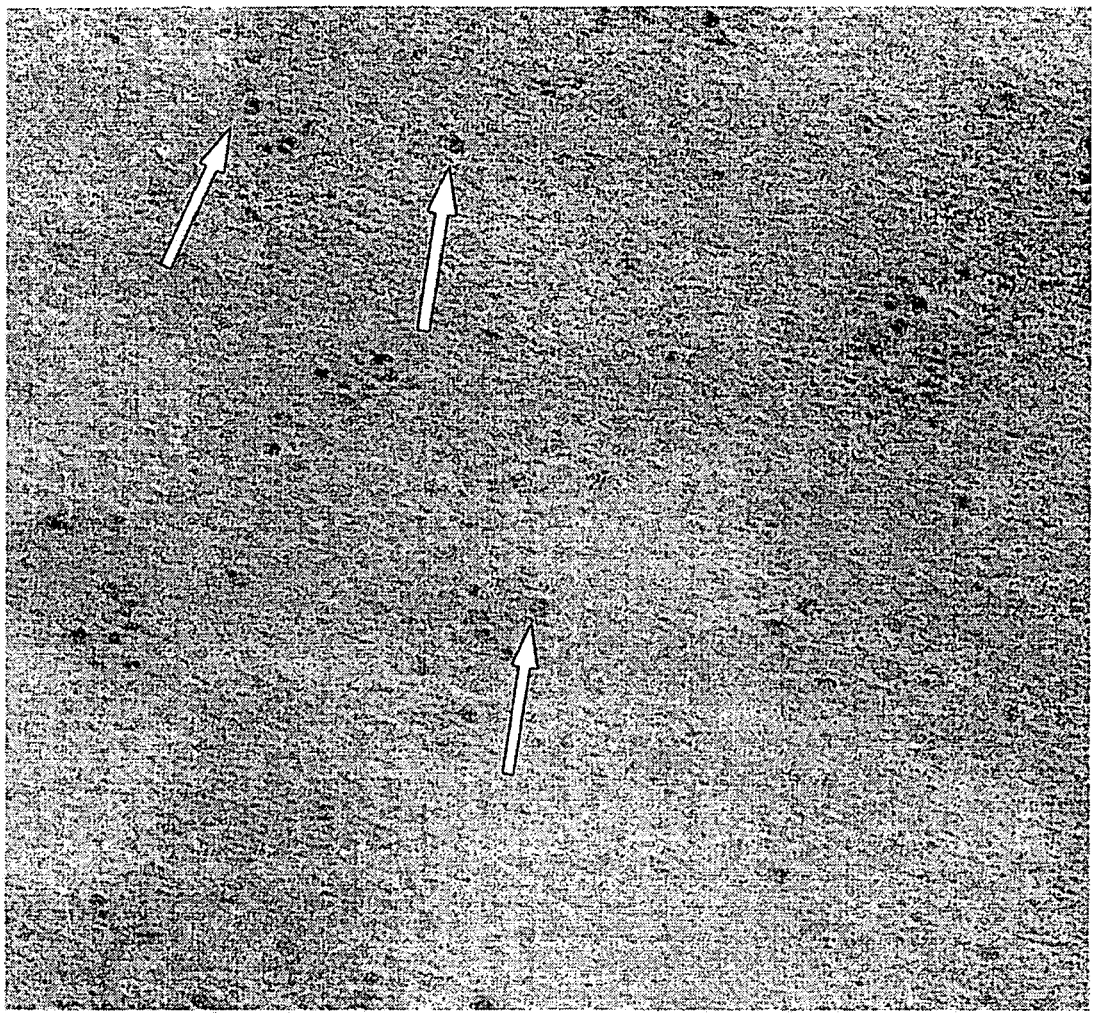
FIG. 2 is a transmission electron micrograph illustrating the state of formation of the zinc oxide-protein complex according to an embodiment of the present invention.

FIG. 2 shows a transmission electron micrograph illustrating the state of formation of the zinc oxide-protein complex.

From this Figure, it is proven that zinc oxide was formed in the holding part of the almost all proteins.

Outline arrow heads in the Figure indicate typical zinc oxide-protein complexes.

Also, whether the substance formed in the holding part of the protein was zinc oxide was ascertained by the measurement of spacing of planes of the crystal structure using a high-resolution transmission electron microscope.

Example 3

In this Example 3, data of preferred zinc ion concentration are demonstrated.

Almost similarly to Example 1, after adding hydrogen peroxide, the ammonia concentration included in the buffer was 16 mM; apoferritin was 0.2 mg/mL; the hydrogen peroxide concentration was 100 mM; and the HEPES solution concentration was 200 mM. The experiment was carried out with the pH value adjusted to be around 6.9.

Then, the study was conducted with varying zinc ion concentration. The zinc ion was supplied in the form of zinc acetate.

The results are shown in Table 3.

TABLE 3

|  | Zinc acetate concentration | | | | | | |
| --- | --- | --- | --- | --- | --- | --- | --- |
|  | 0 mM | 1 mM | 2 mM | 4 mM | 8 mM | 10 mM | 16 mM | 20 mM |
| Formation state of zinc oxide-protein complex | X | ○ | ◎ | ○ | Δ | Δ | Δ | Δ |

("◎": particularly favorable, "○": favorable, "Δ": permissible, "X": unsuitable)

As shown in Table 3, it is proven that the zinc oxide-protein complex could be formed in the range of the zinc ion concentration being 1 mM or greater, 20 mM or less. Particularly, it is proven that the range of the zinc ion concentration being 1 mM or greater, 4 mM or less is preferred in light of the reproducibility and yield.

Example 4

In this Example 4, data of preferred zinc compounds (zinc salts) are demonstrated.

Almost similarly to Example 3, after adding hydrogen peroxide, the ammonia concentration included in the buffer was 16 mM; apoferritin was 0.2 mg/mL; the zinc ion was 2 mM; the hydrogen peroxide concentration was 100 mM; and the HEPES solution concentration was 200 mM. The experiment was carried out with the pH value adjusted to be around 6.9.

In this experiment, zinc acetate, zinc sulfate, or zinc nitrate was used as a source of the zinc ion.

The results are shown in (Table 4).

TABLE 4

| Zinc type | Zinc acetate | Zinc sulfate | Zinc nitrate |
| --- | --- | --- | --- |
| Formation state of zinc oxide-protein complex | ◎ | Δ | ○ |

("◎": particularly favorable, "○": favorable, "Δ": permissible)

As shown in Table 4, any of the zinc compounds could form the complex, however, it is proven that among these three zinc compounds (zinc salts), zinc acetate and zinc nitrate are preferred, and zinc acetate is more preferred.

According to the process for producing a zinc oxide-protein complex of the present invention, nanoparticles of zinc oxide having uniform size can be obtained efficiently.

Furthermore, a semiconductor apparatus having dot bodies including zinc oxide can be obtained by arranging such a protein in a plural number of molecules in a two-dimensional manner, and thereafter baking the protein.

What is claimed is:

1. A process for producing a zinc oxide-protein complex comprising:
    the step a) of preparing a buffer containing a protein having a cavity inside thereof, zinc ion, and ammonia, wherein the protein having a cavity inside thereof is ferritin; and
    a step b) of adding hydrogen peroxide to the buffer so that the concentration of said hydrogen peroxide is 60 mM or greater and 150 mM or less.

2. The process for producing a zinc oxide-protein complex according to claim 1, further comprising a step of
    adding zinc acetate to the buffer prior to the hydrogen peroxide addition step.

3. The process for producing a zinc oxide-protein complex according to claim 2 wherein the concentration of zinc ion after adding the hydrogen peroxide is 1 mM or greater and 20 mM or less.

4. The process for producing a zinc oxide-protein complex according to claim 1, further comprising a step of adding zinc nitrate to the buffer prior to the hydrogen peroxide addition step.

5. The process for producing a zinc oxide-protein complex according to claim 1 wherein the concentration of ammonia after adding the hydrogen peroxide is 8 mM or greater and 360 mM or less.

6. The process for producing a zinc oxide-protein complex according to claim 1 wherein said buffer is a HEPES buffer.

7. The process for producing a zinc oxide-protein complex according to claim 1 wherein said buffer has a pH of 6.9 or greater and 10.4 or less.

8. The process for producing a zinc oxide-protein complex according to claim 1 wherein said ammonia is coordinated with a zinc ion.

9. The process for producing a zinc oxide-protein complex according to claim 8 wherein water is further coordinated with the zinc ion.

* * * * *